United States Patent [19]

Petterson

[11] 4,002,168
[45] Jan. 11, 1977

[54] METHOD OF, AND DISPENSER FOR INTRODUCING AN OPTHALMIC PRODUCT INTO THE OCCULAR CAVITY

[76] Inventor: Tor Petterson, 31248 Palos Verdes Drive West, palos Verdes Penn., Calif. 90274

[22] Filed: Apr. 24, 1975

[21] Appl. No.: 571,294

[52] U.S. Cl. .............................. 128/233; 128/249; 222/421
[51] Int. Cl.² ........................................ A61M 31/00
[58] Field of Search .......................... 128/231–233, 128/248–251; 222/213, 215, 420–422, 481

[56] References Cited

UNITED STATES PATENTS

| | | | |
|---|---|---|---|
| 2,722,216 | 11/1955 | Robbins | 128/233 |
| 2,754,821 | 7/1956 | Burbig et al. | 128/249 |
| 2,898,911 | 8/1959 | Taylor | 128/233 |
| 3,279,466 | 10/1966 | Mings | 128/233 |
| 3,872,866 | 3/1975 | Lelicoff | 128/233 |

FOREIGN PATENTS OR APPLICATIONS

| | | | |
|---|---|---|---|
| 1,208,686 | 10/1970 | United Kingdom | 128/233 |

*Primary Examiner*—Dalton L. Truluck
*Attorney, Agent, or Firm*—A. W. Breiner

[57] ABSTRACT

A dispenser suitable for storing and dispensing an opthalmic product and a method of dispensing the product into an occular cavity while maintaining the dispensing orifice of the dispenser free from contact with the occular cavity is described. The dispenser comprises a container with a cavity for containing a product to be dispensed, pump means, product dispensing valve means, and pressure equalizing valve means. A positioning/guard fixedly secured to the container cooperates therewith to positively position and anthrometically locate the dispensing orifice relative to the occular cavity. The product is dispensed into the eye without loss of product due to inadvertent closing or blinking of the eye as a result of fear of a sharp object and also places the product properly for most effective results.

18 Claims, 26 Drawing Figures

METHOD OF, AND DISPENSER FOR INTRODUCING AN OPTHALMIC PRODUCT INTO THE OCCULAR CAVITY

BACKGROUND OF THE INVENTION

The increase in smog and other impurities in the air in most urban areas coupled with the presence of various types of allergies such as pollen and dust has resulted in the increased need for periodically treating the eyes with various ophthalmic products designed to relieve the discomforts caused by these impurities. In addition, changing consumer life styles have placed an additional strain on eyes; often requiring some kind of relief. For example, activities such as extended viewing of television, driving, close work such as sewing and needlework cause eye strain while outdoor activities where sun and/or wind are involved such as skiing, tennis, golf and sailing cause eye discomfort while activites such as swimming, surfing and smoking are considered more eye irritating. All of the foregoing place an added strain on normal functioning eyes and oftentimes require some kind of relief. Today, there are many over-the-counter ophthalmic products available for temporary relief of these irritations.

In view of the foregoing it is no surprise that recently there has been a substantial growth in the eye hygiene category; particularly in the cosmetic products available. These products have advertising positionings that emphasize "get-the-red-out", soothe and/or cleanse the eyes. Additionally, prescription products available for treating various conditions ranging from infection to diseases have increased significantly.

In the treatment of eyes with either cosmetic products or prescriptive preparations it is imperative that the product dispensed into the eye or occular cavity be sterile. With today's advanced production technology, the production and filling of sterile, ophthalmic products is fairly straight forward. With the sophisticated quality control techniques available today it is most unlikely that a contaminated product would become available to the consumer. However, after these products are filled, distributed and purchased by the consumer there is a substantial risk of their being contaminated during use. For example, in many dispensers available today contamination can result from contaminants in the air being drawn into the dispenser after some product has been dispensed. Such contaminants can then come into contact with the product remaining in the dispenser. This exchange of potentially contaminated air for the product dispensed is one of the factors that has necessitated the use of various preservative additives found in most ophthalmic products today. Such preservatives are described in Table I below and include substances such as disodium edetate, benzalkonium chloride, disodium ethylene diamine tetraacetate and thimerosal. Although these substances are generally used in minute concentrations, ranging from between about 0.001 and about 0.1% by weight; have excellent properties of inhibiting microorganism growth, and produce little known adverse side effects to the eye, it is desirable not to use them.

The presence of these preservatives even at these minute concentrations as well as the presence of the contaminants drawn into the dispenser are particularly troublesome when it becomes necessary to introduce substantial concentrations of the product into the occular cavity. Ironically, the presence of these preservatives and/or contaminants can be most troublesome when the opthalmic product is needed most and used most frequently and/or in high concentrations such as when irrigants, lubricants, miotic neutralizers and antibiotics are used.

That is, the frequent introduction of such "foreign" preservatives and dust, inactivated microorganisms or other contaminants into the eye places an additional burden on the organ necessitating: a high threshold for these substances, flushing of the substance from the eye and/or accommodating these foreign substances. It has been shown that such foreign materials are particularly burdensome to those eyes which are in a weakened condition and require periodic treatment.

Most dispensers in use today for eye hygiene have the general configuration of eye droppers which are held above the eye and squeezed to dispense the drop into the occular cavity. The instructions for their use generally include:
a. tilt the head back,
b. locate dropper over eye,
c. squeeze one or two drops in each eye,
d. blink once or twice, and
e. replace cap on dropper after use.

The traditional design of these types of dispensers includes some form of an elongated point or tip dropper means. It has now been established through extensive consumer research that this dropper design creates a basic hesitancy and oftentimes a fear for the safety of the eye in the mind of the user. This fear is referred by these researchers as the "sharp-stick-in-the-eye" syndrome. This syndrome evidences itself by a general reluctance to use ophthalmic products and/or by an ineptitude in dispensing the product into the eye.

The very nature of many eye problems requiring treatment is that when the eye is to be treated vision is often blurred or impaired. This makes dispensing even more difficult, particularly in locating an eye dropper close to the eye without touching it. If the eye is infected or contagious, contamination of the eye dropper as a result of physically contacting the area being treated becomes a primary concern.

The concern today for ophthalmic dispenser contamination caused by contacting the dropper with foreign substances is paramount. For example, almost without exception the ophthalmic products dispensed by an eye dropper type dispenser in use today, whether over-the-counter or prescriptive, contain the following type of cautionary statement: "Do not touch bottle tip to any surface since this may contaminate the solution". Because of the high risk of contact contamination most manufacturers of ophthalmic products include various preservatives in the product to inhibit the growth of such contaminants. Preservatives similar to those discussed above are generally preferred. Experience has shown that physical contact will probably be made by the dispenser with the contagious area being treated or some other source of contamination at some time during the life of the product.

The difficulty in routinely locating the dropper tip at the right distance from the eye accurately after one eye has been treated is further complicated by the general tendency of most consumers to involuntarily flinch when a drop makes contact with the eye. In fact it is often common, that if more than one drop is administered to the eye at a time, difficulty is experienced in locating the dropper for the second and following drops. The latter will often fall on the eyelid rather than the eye due to a flinching, squinting or other types of involuntary responsive reactions and the failure to locate the dropper accurately.

It has also been observed when conventional squeeze bottledropper type dispensers are used to dispense products into the occular cavity a partial vacuum is created in the dispenser after the product is dispensed. As a result, when compressive force is released from the head of the dropper or the force against the container wall is released, a charge of air enters into the container through the dispensing orifice to replace the product dispensed, thereby equalizing the pressure differential within the container. At this time, if the dropper tip is allowed to remain in the area of the occular cavity it has been observed that various loose contaminants on the skin in the area of the eye can be drawn into the dispensing orifice, eventually contaminating the liquid which is dispensed through the orifice.

Thus, as a result of this air transfer through the dispensing orifice, the internal portion of the dropper tip orifice is generally exposed to contaminants including those generally found in the air, such as bacteria/dust etc., and/or those picked up from contacting the skin around the occular cavity, or those loose contaminants drawn into the container.

In addition to the foregoing, the potential for product contamination during use is further increased by the very mechanical design of most ophthalmic dispensers in use today. That is, the dropper nozzle can be from about less than 1 to about 3 inches long. Most dropperbottles have a dispensing nozzle from between about ½ to 1 inch long. When product is squeezed into the dispensing nozzle only a small portion of that forced into the nozzle is actually dispensed. The remainder returns to the container proper for dispensing at a later time. When in the nozzel, the product has an opportunity to pick up contaminants in the nozzle or at the dispensing orifice. Thus, product dispensed picks up those contaminants present and transfers them to the occular cavity, while product not dispensed picks upon contaminants within the nozzle and returns them to the main solution, contaminating it. A further possibility is that only a portion of a drop is released into the occular cavity while the remainder returns to the main solution, carrying with it contaminants picked up directly from the occular cavity.

OBJECTS OF THE INVENTION

Therefore it is an object of the present invention to provide a method for dispensing a sterile ophthalmic product into the occular cavity.

Another object of the invention is to provide a method of dispensing an ophthalmic product into the occular cavity without creating fear of touching the eye with the dispenser orifice.

A further object of the invention is to provide a method of dispensing ophthalmic products whereby the dispenser is positively positioned and anthrometically located relative to the occular cavity while avoiding contact of the dispenser orifice with said occular cavity.

Still another object of the invention is to provide a method of dispensing sterile ophthalmic products that are substantially free from preservatives.

Yet another object of the invention is to provide a method of dispensing ophthalmic products wherein the product is dispensed by a pump means and the replacement air is filtered prior to entering the dispenser.

A further object of the invention is to provide a method of dispensing ophthalmic products wherein the product is dispensed under metered conditions.

Yet another object of the invention is to provide a method of treating the occular cavity while avoiding interference with normal line of sight and contact by the dispensing orifice with the occular cavity.

A further object of the invention is to provide a method of dispensing ophthalmic products which minimizes contaminants at the dispensing orifice due to air transfer.

Still another object of the invention is to provide a method of dispensing ophthalmic products wherein the dispensing orifice is protected from contact with most objects and surfaces.

An additional object of the invention is to provide a method of dispensing ophthalmic products suitable for children, aged and/or those individuals who have a condition which does not permit them to use eye dropper dispensers without risking making contact with the occular cavity or failing to dispense the product accurately into the occular cavity.

Yet another object of the invention is to provide a method of dispensing ophthalmic products particularly suitable for the routine treatment of the occular cavity, which is infected with a contagion, which avoiding contamination of the dispenser orifice by the contagion.

A further object of the invention is to provide a method for accurately dispensing a prescribed concentration of ophthalmic product into the specific area of the occular cavity.

A further object of the invention is to provide a method of routinely introducing ophthalmic products into an occular cavity fitted with a contact lense.

These and other objects of the invention will become apparent from the following description of the invention in conjunction with the attached drawings wherein.

FIG, 25 is the same view of the dispenser shown in FIG. 24 illustrating removal of the sealing cap means.

SUMMARY OF THE INVENTION

In summary, the present invention relates to methods of dispensing ophthalmic products. More specifically, the present invention is directed to methods of dispensing ophthalmic products into the occular cavity, while maintaining the dispensing orifice thereof free from contact with the occular cavity.

The dispenser comprises:
a. a container for storing product and a pump means for dispensing the product. In a preferred embodiment the container comprises cavity means for storing the product, a pump means for dispensing the product from the cavity, a pressure responsive product dispensing valve means for controlling flow of product to the dispensing orifice and a pressure equalizing valve means for minimizing pressure differential between the cavity and the atmosphere,
b. a dispensing means and a positioning/guard means. In a preferred embodiment, the positioning/guard means positively positions said disepnser and anthropometically locates the dispensing orifice relative to the occular cavity while avoiding contact of said orifice with said occular cavity, and has a ring shaped fitment integral with the container which can be positively positioned around the occular cavity and a dispensing orifice on said fitment in fluid communication with said cavity. In one embodiment, the positioning/guard means is a fitment attached to a conventional eye care dispenser.

The method comprises positively positioning the positioning/guard means of a suitable dispenser around the occular cavity, thereby anthropometically locating the dispensing orifice relative to said cavity and activating the pump means.

THE CONTAINER

The container comprises a cavity means which can be made in various sizes and shapes is designed to store the ophthalmic product. Generally, the cavity means will contain from between about 5 to about 150 cc of the product.

Figures 16, 17, 18, 19, 20:
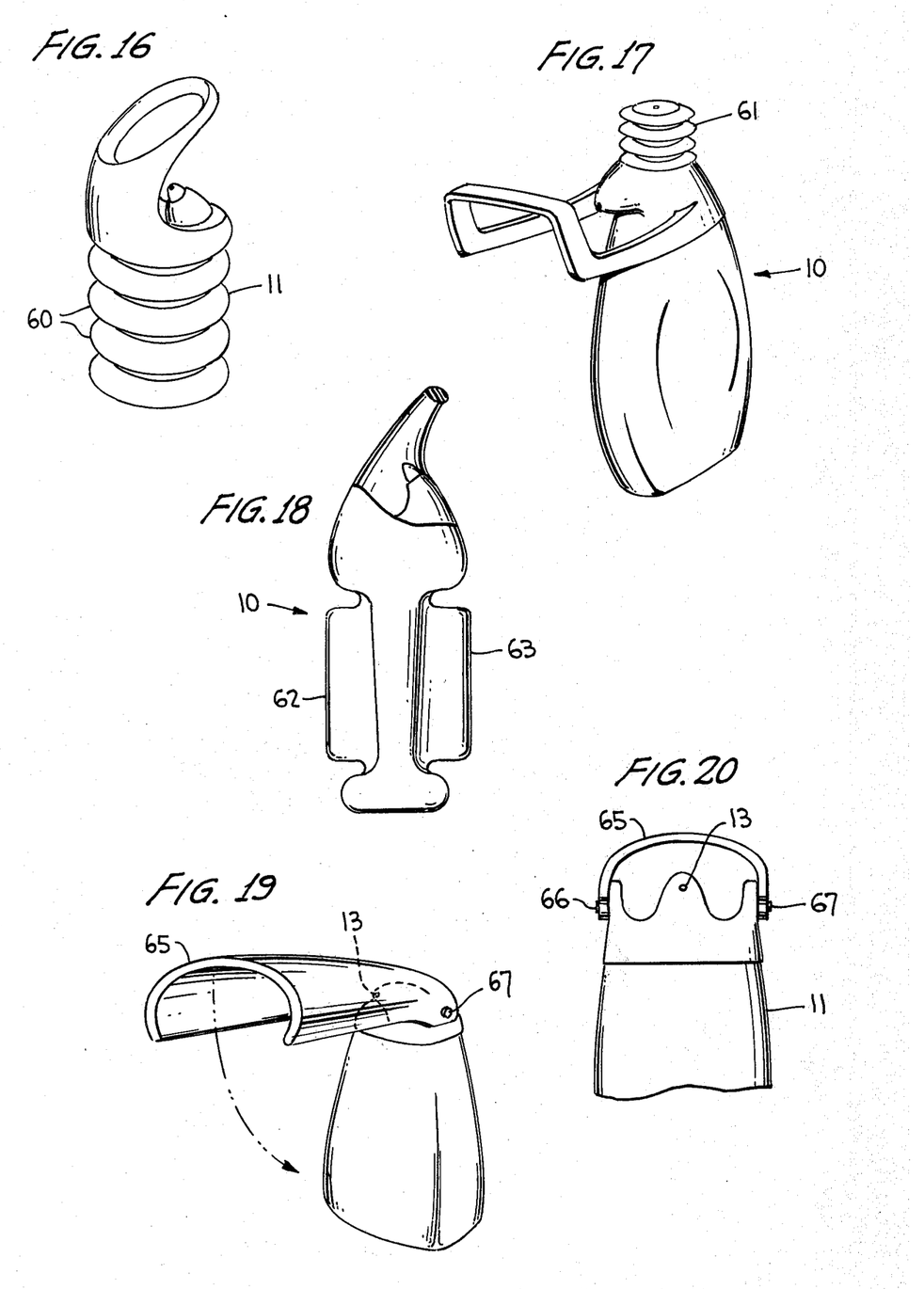
FIGS. 16, 17 and 18 are elevational views of dispensers illustrating various pump means that can be employed.
FIGS. 19 and 20 are a perspective and front elevational views respectively of a dispenser of the invention illustrating a collapsible overcap/seal/guard/positioning embodiment.

The shape of the container is generally such that the pump means thereof can be held conveniently between the thumb and forefinger. The pump means is located in the cavity and serves to displace some of the ophthalmic product from the container through a pressure responsive valve provided with a dispensing orifice. The pump means generally requires a force of from between about 200 and about 1000 gm and can produce temporary increases of pressure from between about 1 and 15 lbs. The pump can comprise a flexible wall of the cavity means which is depressable sufficiently to displace a portion of the product shown in FIG. 4. Alternatively, the pump can comprise an elastomeric member inserted in the cavity wall as illustrated in FIG. 18. The flexible wall can also be in the form of an accordion type pump means as shown in FIGS. 16 and 17.

Figures 3, 4, 6:
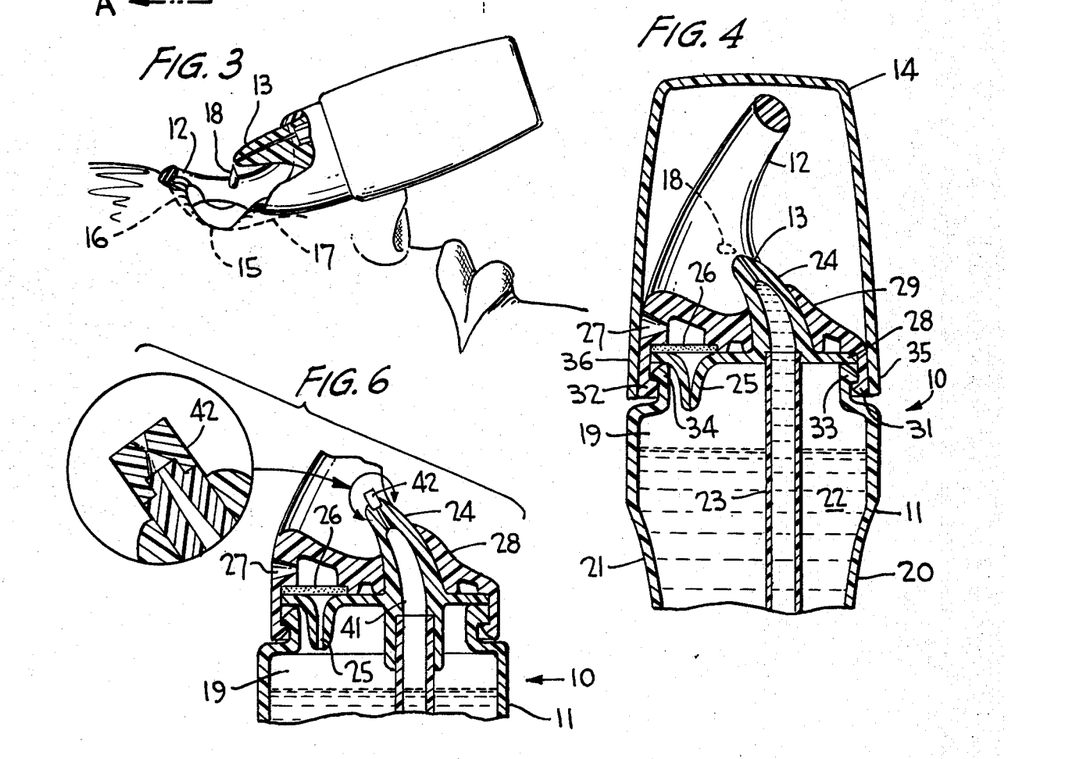
FIG. 3 is a cross section side view of the dispenser shown in FIG. 1 positioned around the occular cavity illustrating the relative position of the dispensing orifice to the occular cavity while a drop is being dispensed.
FIG. 4 is a sectional elevational view of the dispenser shown in FIG. 1 taken along line AA illustrating the cavity means, pump means, product dispensing valve and pessure equalizing valve while product is being dispensed through the dispensing orifice.
FIG. 6 is a sectional elevational view of the dispenser shown in FIG. 5 illustrating the pressure equalizing valve means in the open condition.

The pressure responsive product dispensing valve is located generally in the upper portion of the cavity and is so designed that upon the application of pressure to the cavity it opens to allow some of the product to be dispensed. This valve can generally be described as a one-way valve which will allow product to be dispensed from the container but will not allow excess product and/or air to enter the cavity. These types of valves are generally referred to as duckbill valves. For the purpose of the invention this one-way valve can be a separate component incorporated into the body of the container as a part of a gasket as shown in FIG. 6, or it can be a flap type arrangement molded into the container body. The one-way feature of this valve is critical to the present invention. That is, since this valve does not allow product and/or air to return to the container once it has passed through the valve, the opportunity for contamination of sterile product stored in the container is minimized. The valve is suitable for dispensing drops as well as sprays. This embodiment of the invention is illustrated in FIG. 6.

Figure 7:
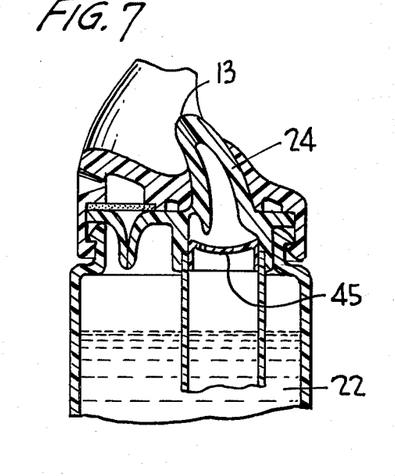
FIG. 7 is a sectional elevational view of a dispenser illustrating a metering dispensing valve means.

In a preferred embodiment of the invention the pressure responsive product dispensing valve is provided with a metering means which is designed to control the amount of product dispensed. Such a metering means is illustrated in FIG. 7 and comprises a ball or sphere positioned in the dip tube leading to the valve. This metering valve can be varied to dispense from between about 0.1 and about 1 gram of product per each pumping of the pump means. The pressure responsive product dispensing valve functions not only to control the one-way dispensing of product and exclusion of contaminants entering the cavity, but also can be designed to control the size of the drop dispensed. For example, the cross section dimension of the dispensing orifice in conjunction with the amount of force applied to dispense the product will define the size of the drop released from the orifice. Generally, the drop size preferred is about 0.2 grams. However, there are instances where larger or smaller drops are preferred and these can be obtained by altering the dispensing orifice and pump pressure appropriately. Similarly, if sprays are to be dispensed, appropriate mechanical breakup means can be used to control the particle size and particle size distribution of the spray.

The pressure equalizing valve means is located generally in the upper portion of the cavity. It is responsive to the pressure differential that results from dispensing product from the cavity by the pump means. That is, when product has been forced out of the cavity by activating the pump means a pressure differential or partial vacuum is created inside the cavity. In order to compensate for this pressure differential and return the cavity to a pressure equal to that outside the container, the pressure equalizing valve means responds by opening and allowing air to enter the cavity from outside the container. Similar to the product dispensing valve, it can be a one-way valve, such as a duckbill valve which allows air to pass into the container. This valve means can be a separate component or incorporated in the gasket and positioned in the upper end of the cavity as shown in FIG. 6 or it can be a flap means or slit incorporated in the upper wall of the cavity.

In a preferred embodiment of the invention the pressure equalizing valve means is provided with a filter means which functions to filter the air that enters the cavity after product has been evacuated. The filter is capable of screening out the major contaminants of air such as dust, pollen and various microorganisms ranging from single cell substances to various complex substances such as virus, spores, bacteria and other microflora. Those filter substances which allow air to pass through but restrict contaminants down to about ½ micron are particularly well suited for the present invention. Suitable filter materials include various microporus substances such as permeable membranes including paper, leather, cotton fiber, nonwettable porous materials such as teflon membranes, microporous materials such as ceramic and sintered metal substances with appropriate sized passages. These filter materials are capable of filtering out contaminants in the air from between about 0.5 and about 20 microns.

Figure 8:
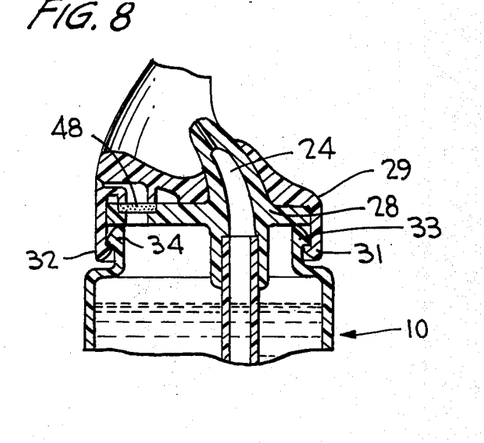
FIG. 8 is a sectional elevational view of a dispenser illustrating a nonwettable pressure equalizing means.

In a particularly preferred embodiment of the invention the filter material does not allow the ophtahlmic product to pass through. In this embodiment of the invention the filter material can be fabricated from a substance that is nonwettable by the ophthalmic product or alternatively, the filter means can be combined with a one-way pressure equalizing valve means as shown in FIG. 6. When the filter means is constructed of a substance that is nonwettable by the ophtahlmic product there is no need to provide a separate one-way valve means as shown in FIG. 8. Thus, the location of the dispensing orifice relative to the pressure equalizing valve means is not critical since the product cannot escape through the latter.

The rate of air flow through the pressure equalizing valve is such that the pressure differential resulting from dispensing the product initially is compensated for prior to initiating a second dispensing. A flow rate of from between about 0.5 and about 500 cc/cm$^2$/sec. Generally this pressure equalizing is achieved in from about 0.1 to about 2 seconds.

POSITIONING/GUARD MEANS

The positioning/guard means can be an integral member of the dispenser or it can be a fitment that is attached to the container and positioned around the dispensing orifice.

The positioning/guard means is tactily positioned against the area around the occular cavity and anthropometically locates the dispensing orifice of the container relative to the occular cavity while avoiding contact of orifice with the occular cavity. Additionally, the positioning/guard means protects the dispensing orifice from coming into contact with any generally flat or arcuate surface. It has been found that only those objects which are probe-like and/or of size sufficient to fit within the ring of the positioning/guard means can make contact with the dispensing orifice. Thus, except for misuse, under normal use, the dispensing orifice will not make contact with objects during the useful life of the dispenser. The advantages in avoiding inadvertent contact of the dispensing orifice with contaminants are significant especially when compared to dispensers available at present.

For the purposes of the present invention occular cavity is defined as that area immediately surrounding the eye and including the eye.

The positioning/guard means comprises a ring shaped integral member of the dispenser containing the dispensing orifice and in fluid communication with the container or a fitment attached to the container positioned around the dispensing means. In either case the positioning/guard means is positively positioned around the occular cavity by pressing it against the area defined by the eyebrow and the upper cheek. At the same time, the dispensing orifice can be anthropometically located relative to the occular cavity. For example, the dispensing orifice is positioned at a predetermined distance from the eye as shown in FIG. 3. Generally the dispensing orifice is positioned no closer than about 10 mm from the closest surface of the occular cavity and no further than about 100 mm from the occular cavity. The distance the dispensing orifice is located from the occular cavity is in part determined by the type of product to be dispensed as well as the size of each drop and the number of drops dispensed. It has been found that the proximity of the dispensing orifice to the occular cavity is particularly critical when treating various contagious conditions to insure that contamination of the dispenser and/or product is avoided.

The positioning/guard means is generally described as ring shaped. However, it should be understood that the positioning/guard means need only be capable of being positioned around the occular cavity by contacting at least a portion of the brow and upper cheek areas. As such, the positioning/guard means need not be a continuous ring and can be a series of bars similar to those shown in FIGS. 13, 14 and 15. The general configuration of the positioning/guard means will in part be determined by the type of product to be dispensed and the ophthalmic condition being treated. This is illustrated further in Table I.

In a preferred embodiment of the invention the positioning/guard means is generally ring shaped and capable of being positioned around the occular cavity without creating fear in the mind of the user of touching the eye with the dispenser orifice. These types of dispensers are shown in FIGS, 1, 2, and 9–12.

In another preferred embodiment of the invention the positioning/guard means when positioned around the occular cavity does not interfere with the normal line of sight. It has now been discovered that those positioning/guard means which do not interfere with the line of sight of the user, while bein positively positioned around the occular cavity, provide the user with a confidence and freedom from fear previously unattainable when dispensing ophthalmic products.

The positioning/guard means of the present invention provides additional advantages for ophtahlmic dispensers previously not available. For example, the general configuration of the positioning/guard means can be varied along with the angle of the positioning means to the container axis. This is described in Table I. It should be understood that the location of the dispensing orifice on the positioning/guard means can be varied so the product dispensed can be introduced into a specific area of the occular cavity with great precision and accuracy while requiring little dexterity of the person using the product. This feature is particularly advantageous with products such as irrigants, lubricants, miotic neutralizers and anesthetics. Thus, it can be appreciated that dispensers of the present invention can be designed for accurately and routinely introducing product into specific areas of the eye including tear ducts, conjunctival sac and the iris/pupil area.

A particularly novel and unexpected advantage of the dispensers of the present invention is that they can be used by people with little dexterity such as young children or the infirmed or aged. In addition, the dispenser can be used by people with eye conditions which interrupt vision so that heretofore they were unable to locate the dispenser orifice without contacting the eye.

DESCRIPTION OF THE DRAWINGS

Figures 1, 2:
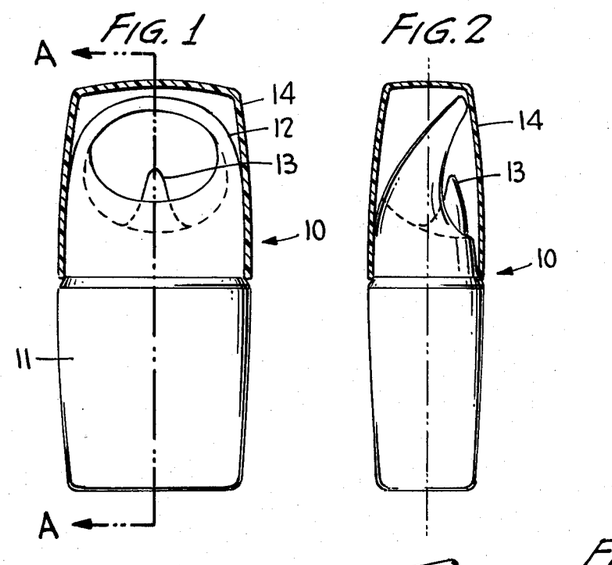
FIG. 1 is a front elevational view of a dispenser of the invention illustrating the relative position of the dispensing orifice to the positioning/guard means.
FIG. 2 is a side elevational view of the dispenser shown in FIG. 1 further illustrating the relative position of the dispensing orifice to the positioning/guard means.

Referring to FIG. 1 of the drawing, an ophtahlmic dispenser constructed in accordance with the present invention is generally designated by the reference numeral 10 and includes a container 11, provided with an integral generally ring shaped positioning/guard means 12 dispensing orifice 13 and overcap 14.

Referring to FIG. 2, the relative position of dispensing orifice 13 to the axis of container 14 is illustrated. The relationship of dispensing orifice 13, to guard means 12, is further illustrated in FIG. 3, which shows the distance between the dispensing orifice and the nearest surface of the occular cavity, designated as 15. FIG. 3 further illustrates the positive, tactile positioning of guard means 12 against the general area surrounding the occular cavity designated as 16 and 17. FIG. 3 further illustrates that drop 18 will be free from orifice 13 before it makes contact with occular cavity 15, thereby avoiding contamination of orifice 13.

Referring to FIG. 4, dispenser 10 is shown with container 11, having walls 20 and 21 depressed to create a pumping action thereby forcing product 22 from cavity 19 up through dip tube 23, into product dispensing valve means 24, and out orifice 13, and drop 18. Dip tube 23 can be excluded, with product 22 pumped directly into valve means 24. Dispenser 10 is provided with pressure equalizing valve means 25, which is shown closed, filter means 26, and air inlet means 27. In this embodiment of the invention, dispensing valve 24 and pressure equalizing valve 25 are duckbill-type valves molded into gasket means 28, which is fitted between container cap means 29 and container 11. Container cap means 29 includes positioning/guard means 12, and is secured to container 11, by detents 31 and 32 which engage container detents 33 and 34 respectively. Dispenser 10 is provided with overcap 14, which engages cap 29 at 35 and 36 respectively and protects positioning/guard means 12, and orifice 13 from contamination.

Figure 5:
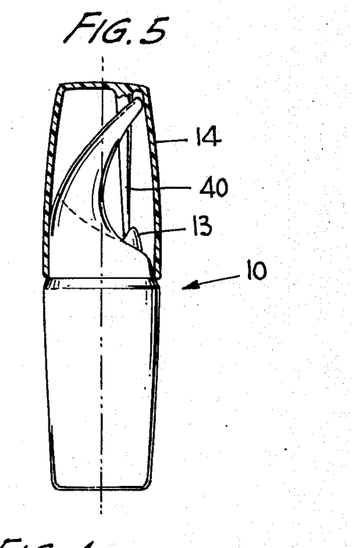
FIG. 5 is a side elevational view of a dispenser of the invention illustrating an overcap/plug arrangement for maintaining the dispensing orifice free from contamination by dust, etc.

Referring to FIG. 5, dispenser 10 is provided with overcap 14 which is provided with plug means 40. Plug means 40 engages dispenser orifice 13, of dispensing valve means 24, to provide a positive closure of the orifice during storage. Plug means 40 is particularly effective in maintaining orifice 13 in an open condition when isotonic solutions are dispensed.

Referring to FIG. 6, dispenser 10 is shown shortly after product has been dispensed and replacement air is entering container 11. Dispenser 10 is provided with cap 28 which contains discharge channel 41 and spray head 42. Channel 41 is in fluid communication with product dispensing valve 24, shown in the closed position. Pressure equalizing means 25, is shown in the open position and allows air passing from air inlet 27, through filter means 26, to enter cavity 19, thereby equalizing the pressure inside the dispenser with that outside.

Referring to FIG. 7, dispenser 10 is provided with product dispensing valve means 24, which contains metering means 45, which controls the amount of product 22, dispensed through orifice 13.

Referring to FIG. 8, dispenser 10, is provided with gasket means 28, secured to container 11 by cap means 29, which is secured to the container by the engagement of detent means 31 and 32 with detent means 33 and 34 respectively. Gasket 28 is provided with non-wettable, pressure equalizing, filter means 48 and product dispensing valve means 24.

Referring to FIGS. 1, 2, and 9–15, it is apparent that the configuration of the positioning/guard means 12 can be modified to accommodate the various ophthalmic products to be dispensed. These configurations can range from round, shown in FIG. 11 to the oval 50, shown in FIGS. 9, 10, and 12, to the partial ring 51, shown in FIG. 13 to the contact bars 52, 53, 54, and 55, shown in FIGS. 14 and 15 respectively. Such configurations are further discussed in Table I.

Figure 13:
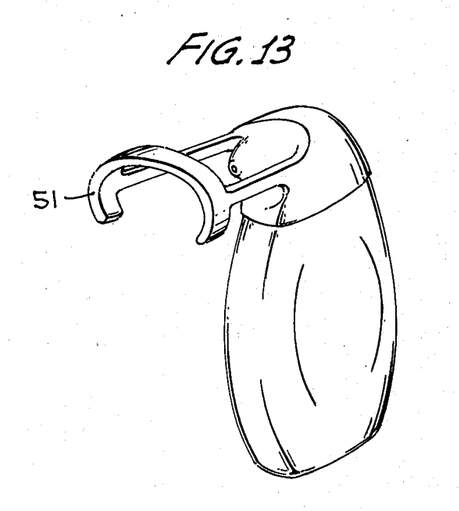
Figure 14:
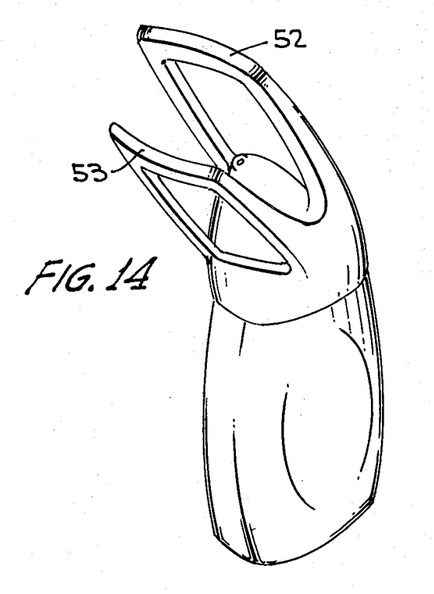
Figure 15:
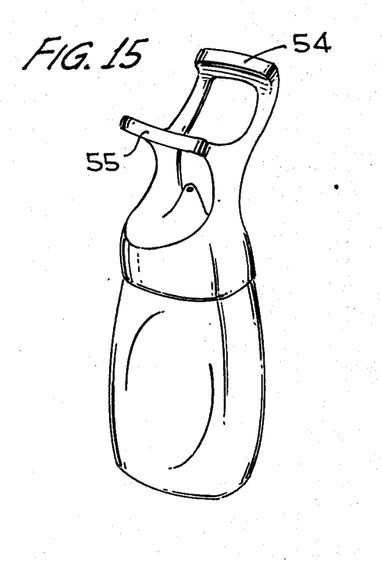

Additionally, these dispensers illustrate that the angle of the positioning means to the container axis can vary from 0° to 90° off axis depending on the product to be dispensed and the ophthalmic condition to be treated. For example, positioning means 12 of FIG. 2 is approximately 60° off axis, whereas positioning means 12 of FIG. 12, and contact bars 54 and 55 of FIG. 15, are approximately 0 degrees off axis, while partial ring 51 of FIG. 13 is 90° off axis.

Referring to FIGS. 16, 17 and 18 it is apparent that dispenser 10 can be provided with varying types of pump means. For example, in FIG. 16 container 11 is provided with accordion walls 60 which are depressible axially to provide a dispensing force. Alternatively, in FIG. 17, the pump type cap 61 of dispenser 10 provides sufficient internal pressure to dispense the product. In FIG. 18, pump means 62 and 63 of dispenser 10 displaces product by a squeezing type action between forefinger and thumb at 62 and 63 respectively.

Referring to FIGS. 19 and 20, collapsible seal/guard/positioning means 65 is hinged at 66 and 67, so it can be collapsed against container 11 thereby providing a seal of orifice 13. When unfolded, means 65 can be positioned around the occular cavity and anthrometically locate dispensing orifice 13 relative to the occular cavity.

Figures 21, 22, 23:
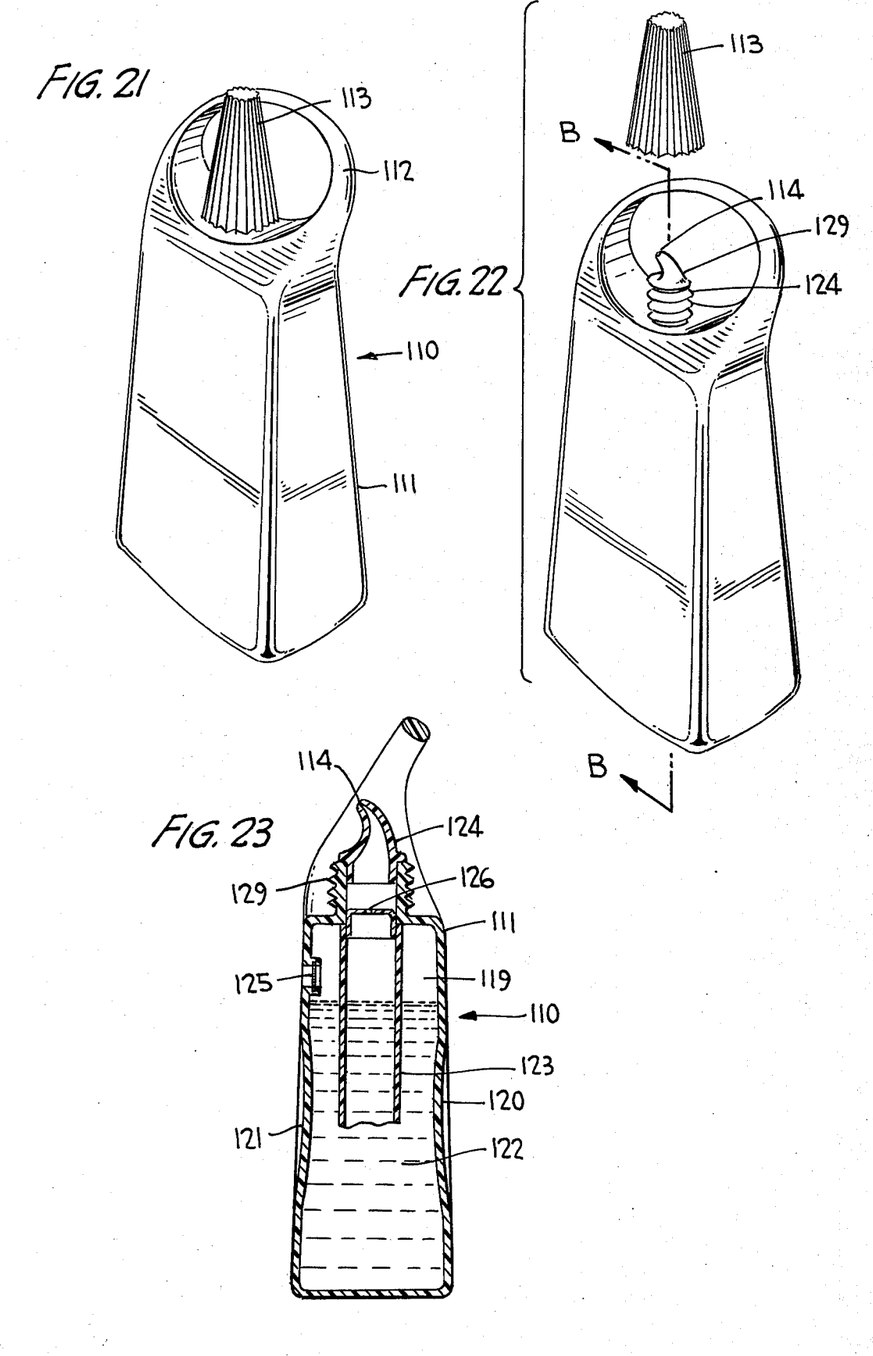
FIG. 21, is a partial front elevational view of a dispenser of the invention illustrating the positioning/guard means integral with the container.
FIG. 22, is the same view of the dispenser shown in FIG. 21 illustrating removal of the sealing cap means.
FIG. 23, is a cross section side view of the dispenser shown in FIG. 22 taken along the line AA illustrating a one-way dispensing valve means, a nonwettable pressure equalizing means, and a product metering means.

Referring to FIG. 21 of the drawing, an ophthalmic dispenser constructed in accordance with the present invention is generally designated by the reference numeral 110 and includes a container 111, provided with an integral generally ring shaped positioning/guard means 112 dispensing means not shown, and seal cap means 113 which threadedly engages the base of the dispensing means, not shown.

Referring to FIG. 22, the relative position of dispensing means 124 and dispensing orifice 114 to the axis of container 111, is illustrated. The relationship of dispensing means 124 to guard means 112, is also illustrated.

Referring to FIG. 23, dispenser 110, is shown with container 111, having walls 120 and 121 depressed to create a pumping action thereby forcing product 122 fron cavity 119 up through dip tube 123, into product dispensing means 124, and out orifice 114. Dip tube 123, can be excluded, with product 122 pumped directly into dispensing means 124. Dispenser 110, is provided with pressure equalizing means 125, which is a nonwettable permeable membrane. In this embodiment of the invention, dispensing means 124 is a duckbill-type valve inserted into container 111. In FIGS. 21–23 dispenser 110 is provided with sealing cap means 113 which threadedly engages the outer base 129 of dispensing means 124 and protects dispensing orifice 114 from contamination. Sealing cap means 113 could be provided with a plug means (not shown) which engages dispenser orifice 114 of dispensing means 124, to provide a positive closure of the orifice during storage. Such a plug means would be particularly effective in maintaining orifice 114 in an open condition when isotonic solutions are dispensed. Product dispensing means 24 contains metering means 126 which controls the amount of product 122, dispensed through orifice 114 with each pumping action.

Figure 24:
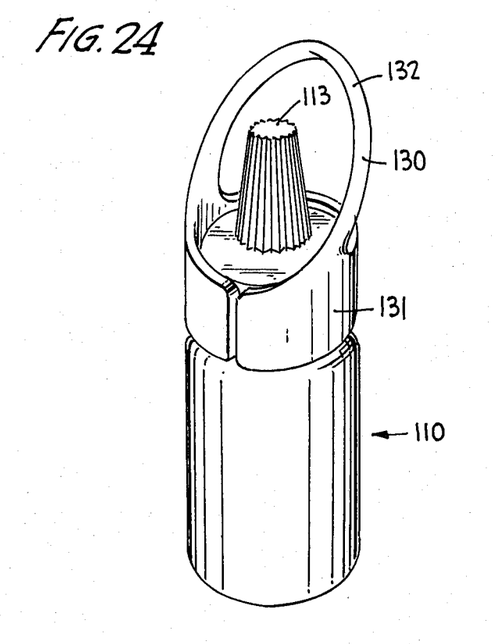
FIG. 24 is a partial front elevational view of a dispenser of the invention illustrating a positioning/guard means fitment.
Figure 25:
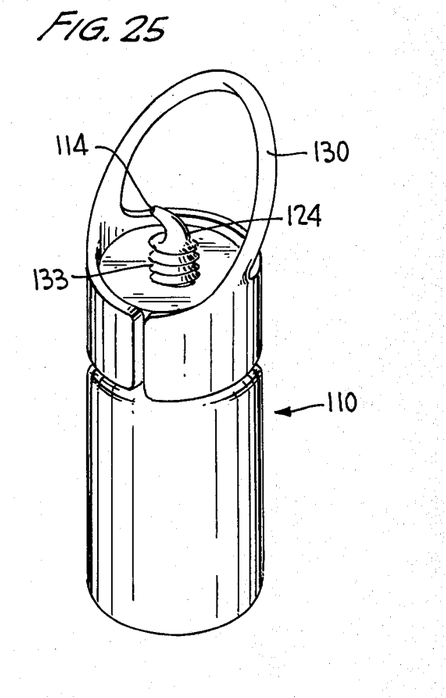
Figure 26:
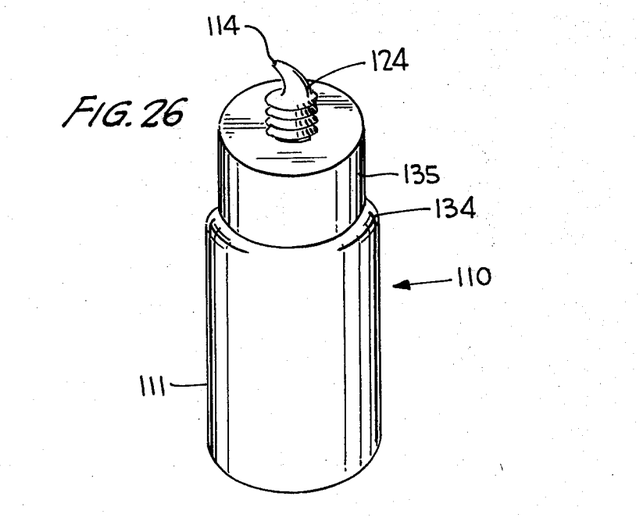
FIG. 26 is the same view of the dispenser shown in FIG. 24 illustrating removal of the positioning/guard means fitment.

Referring to FIGS. 24-26, an ophthalmic dispenser 110 of the invention is shown with a positioning/guard means fitment 130 secured to the dispenser by means of inwardly biased securing band 131. Fitment 130 is provided with ring-shaped positioning/guard means 132, which is located around dispensing means 124 and orifice 114. Dispensing means 114, is covered by seal cap means 113, which is threadedly secured thereto by means of threads 133.

Container 111 of dispenser 110 is provided with upper shoulder 134 and neck 135, which are engaged by band 131 thereby securing fitment 130 to dispenser 110. Thus, essentially any conventional eye care dispenser could conceivably be modified with the addition of an appropriate positioning/guard means to provide an ophthalmic dispenser of the invention.

The dispensers of the invention can be used for a variety of ophthalmic products as described in the illustrative examples in Table I below.

The advantages of the present invention described in Table I below include the usee of sterile ophtahmic products which do not require preservatives to maintain sterility. Additional advantages include maintaining the dispensing orifice free from contamination; filtering the replenishment air so that it does not contaminate the product; and not allowing dispensed product to return to the container cavity and are described in Table I.

TABLE 1

Figures 9, 10:
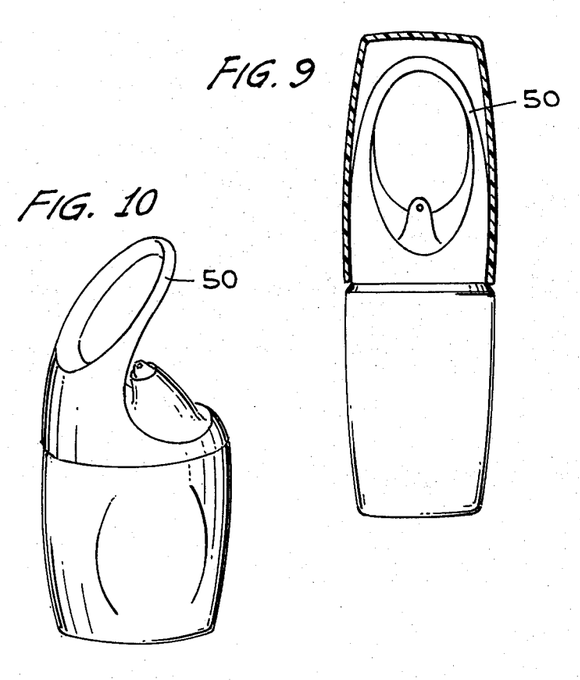
FIGS. 9–15 are elevational views of dispensers of the invention illustrating various configurations of the positioning/guard means and the varying angles of the positioning/guard means to the container axis.

| EXAMPLE | 1 | 2 |
|---|---|---|
| PRODUCT | Antibacterial/Antibiotic | Antibacterial/Antibiotic |
| CONTAINER | 10cc plastic dropper bottle | 10cc plastic container similar to that shown in FIG. 1. |
| CONDITION | Diseases due to microorganism infections, such as, nonpurulent blepharitis, blepharo-conjunctivitis, nonpurulent conjunctivitis | (Same as example 1) |
| COMPOSITION/ ACTIVE INGREDIENTS (% by weight) | Sodium sulfacetamide (10) Prednisolone acetate (0.2) Phenylephrine HCL (0.12) Polyvinyl alcohol (1.4) Antipyrine (0.1) Sodium thiosulfate (0.2) Hydrochloric acid to pH 6.8 | (Same as example 1) |
| PRESERVATIVE/ FILTER (% by weight) | Disodium edetate (0.1) Chlorobutanol (0.5) | None Filter - 0.5 micron in combination with one way valve |
| POSITIONING/GUARD MEANS GENERAL CONFIGURATION (angle of positioning means to container axis) | None | Horizontal oval (60° off axis) |
| ADMINISTRATION/ DOSAGE | 1 drop, two to four times daily depending on severity of the condition | (Same as example 1) |
| PURITY OF PRODUCT IN CONTAINER: | | |
| AT TIME OF FILLING | Sterile | Sterile |
| AFTER 5 DOSES | Sterile (some inactivated air borne microorganisms generally present) | Sterile (no air borne bacteria present) |
| WITH 10% LEFT IN CONTAINER | Sterile (provided dropper tip has not contacted infected area) | Sterile - dispenser means prevented from contacting infected area by guard/positioning means |
| EXAMPLE | 3 | 4 |
| PRODUCT | Lubricant | Lubricant |
| CONTAINER | 15cc plastic dropper bottle | 15cc plastic container similar to that shown in FIG. 10 |
| CONDITION | Dry eyes such as in keratitis sicca or where natural tears are absent or inadequate | (Same as Example 3) |
| COMPOSITION/ ACTIVE INGREDIENTS % by weight) | Polyvinyl alcohol (1.4) Sodium chloride to pH 6.8 | (Same as Example 3) |

TABLE 1-continued

| | | |
|---|---|---|
| PRESERVATIVE/ FILTER % by weight) | Chlorotutanol (0.5) | None - nonwettable filter - 0.5 micron |
| POSITIONING/GUARD MEANS GENERAL CONFIGURATION angle of positioning means to container axis) | None | Narrow vertical oval (75° off axis) |
| ADMINISTRATION/ DOSAGE | 1-2 drops several times daily or as needed | (Same as Example 3) |
| PURITY OF PRODUCT IN CONTAINER: | | |
| AT TIME OF FILLING | Sterile | Sterile |
| AFTER 5 DOSES | Sterile (some inactivated microflora present) | Sterile (no air borne microorganisms present) |
| WITH 10% LEFT IN CONTAINER | Sterile (provided dropper does not contact the eye or foreign surfaces) | Sterile, dispenser means prevented from contacting tear duct area by guard/positioning means |
| EXAMPLE | 5 | 6 |
| PRODUCT | Lubricant | Lubricant |
| CONTAINER | 15cc plastic dropper bottle | 15cc plastic container similar to that shown in FIG. 1 |
| CONDITION | Eye irritation due to deficient tear production | (Same as Example 5) |
| COMPOSITION/ ACTIVE INGREDIENTS (%) by weight) | Sterile, isotonic clear ophthalmic composition containing balanced amounts of sodium and potassium ions, a cellulose derivative for viscosity control, pH and viscosity of tears | (Same as Example 5) |
| PRESERVATIVE/ FILTER (% by weight) | Benzalkonium chloride (0.01) Disodium edetate (0.05) | None - filter 0.5 micron, in combination with one-way valve |
| POSITIONING/GUARD MEANS GENERAL CONFIGURATION (angle of positioning means to container axis) | None | Narrow vertical oval (75° off axis) |
| ADMINISTRATION/ DOSAGE | 1-2 drops three to four times daily | (Same as Example 5) |
| PURITY OF PRODUCT IN CONTAINER: | | |
| AT TIME OF FILLING | Sterile | Sterile |
| AFTER 5 DOSES | Sterile (some denatured microflora present) | Sterile (no contamination present) |
| WITH 10% LEFT IN CONTAINER | Sterile - to maintain sterility avoid touching dropper tip to eyelids or other surfaces | Sterile - dispenser means protected by guard/positioning means and overcap means |
| EXAMPLE | 7 | 8 |
| PRODUCT | Miotic/neutralizer | Miotic/neutralizer |
| CONTAINER | 15cc glass stopped bottle | 15cc plastic container similar to that shown in FIG. 1 |
| CONDITION | Chronis, open-angle glaucoma; mydriasis or cycloplegia following ophthalmoscopy or surgery | (Same as Example 7) |
| COMPOSITION/ ACTIVE INGREDIENTS (% by weight) | Hypoallergenic, sterile, buffered, isotonic solution of pilocurpine HCL, and sodium biphosphate, sodium phosphate, sodium chloride as required to achieve isotonicity | (Same as Example 7) |
| PRESERVATIVE/ FILTER (%) by weight) | Benzalkonium chloride (0.01) Disodium edetate (0.01) | None - filter with non-wettable surface |
| POSITIONING/GUARD MEANS GENERAL CONFIGURATION (angle of positioning in means to container axis) | None | Horizontal oval (60° off axis) |
| ADMINISTRATION/ DOSAGE | 1-2 drops in the affected eye up to six times daily | (Same as Example 7) |
| PURITY OF PRODUCT IN CONTAINER: | | |
| AT TIME OF FILLING | Sterile | Sterile |
| AFTER 5 DOSES | Sterile | Sterile - no microflora present |
| WITH 10% LEFT IN CONTAINER | Sterile - difficult to maintain because of tendency to contact dropper tip to eyelid and/or area around the eye | Sterile - dispenser means protected by guard/positioning means |

TABLE 1-continued

| EXAMPLE | 9 | 10 |
|---|---|---|
| PRODUCT | Vasoconstrictor | Vasoconstrictor |
| CONTAINER | 30cc plastic squeeze bottle | 30 cc plastic squeeze container as shown in FIG. 10 |
| CONDITION | Conjunctival hyperemia and allergic conjuctivitis evidenced by burning, itching, lacrimation due to allergic and eye irritating conditions | (Same as Example 9) |
| COMPOSITION/ ACTIVE INGREDIENTS (% by weight) | Sterile, stable solution containing tetrahydrozoline hydrochloride (0.05) Sodium chloride, boric acid, sodium borate | (Same as Example 9) |
| PRESERVATIVE/ FILTER (% by weight) | Benzalkonium chloride (0.01) Disadium ethylenediamine tetraacetate (0.1) | None - filter with one-way valve |
| POSITIONING/GUARD MEANS GENERAL CONFIGURATION angle of positioning means to container axis) | None | Backwards slanted horizontal oval (70° off axis) |
| ADMINISTRATION/ DOSAGE | 1-2 drops in each eye as needed | (Same as example 9) |
| PURITY OF PRODUCT IN CONTAINER: | | |
| AT TIME OF FILLING | Sterile | Sterile |
| AFTER 5 DOSES | Sterile (some inactivated bacteria present) | Sterile |
| WITH 10% LEFT IN CONTAINER | Sterile - provided no contact made with the conjunctival sac & surrounding area | Sterile |

Figure 11:
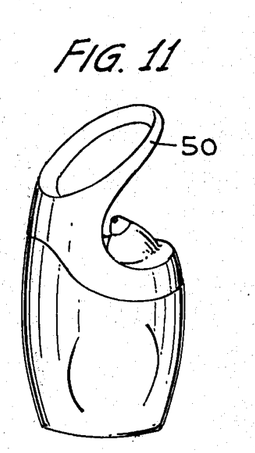
Figure 12:
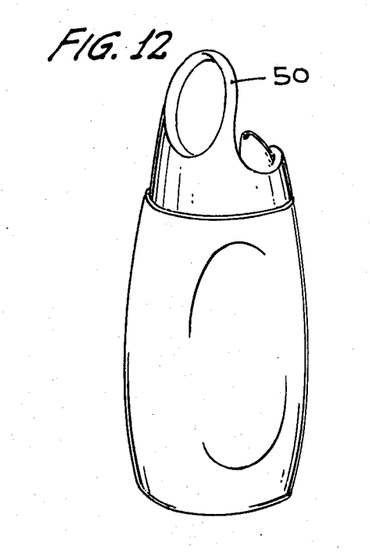

| EXAMPLE | 11 | 12 |
|---|---|---|
| PRODUCT | Antibacterial | Antibacterial |
| CONTAINER | ½oz. bottle with dropper | ½oz. plastic container such as shown in FIG. 11 |
| CONDITION | Conjunctivitis, blephartis, dacryocystitis corneal ulcer & other external eye infections due to susceptible microorganisms | (Same as Example 11) |
| COMPOSITION/ ACTIVE INGREDIENTS (% by weight) | Sterile, isotonic solution with a physiological pH containing sulfisoxazole in the form of the diolamine salt | (Same as Example 11) |
| PRESERVATIVE/ FILTER % by weight) | Phenylmecuric nitrate (1:100,000) | None, filter with one-way valve |
| POSITIONING/GUARD MEANS GENERAL CONFIGURATION angle of positioning means to container axis) | None | Anthroprometic oval approx. 1¼inches in diameter (65% off axis) |
| ADMINISTRATION/ DOSAGE | 2-3 drops in the eye, three or more times daily | (Same as Example 11) |
| PURITY OF PRODUCT IN CONTAINER: | | |
| AT TIME OF FILLING | Sterile | Sterile |
| AFTER 5 DOSES | Sterile - some contamination due to contacting dropper tip to infected area. | Sterile - no contamination |
| WITH 10% LEFT IN CONTAINER | Sterile - but some contamination due to contact of dispenser with infected area | Sterile |

| EXAMPLE | 13 | 14 |
|---|---|---|
| PRODUCT | Cyclopegic Mydriatic | Cyclopegic Mydriatic |
| CONTAINER | 15 ml dropper bottle | 15 ml container as shown in FIG. 1 |
| CONDITION | — | — |
| COMPOSITION/ ACTIVE INGREDIENTS % by weight) | Cyclopentolate hydrochloride, Boric acid, potassium chloride, sodium carbonate | (Same as Example 13) |
| PRESERVATIVE/ FILTER % by weight) | Benzalkonium chloride | None - Filter |
| POSITIONING/GUARD MEANS GENERAL CONFIGURATION angle of positioning means to container axis) | None | Circle useful for horizontal and vertical applications (60° off axis) |

TABLE 1-continued

| | | |
|---|---|---|
| ADMINISTRATION/ DOSAGE | One drop in each eye | (Same as Example 13) |
| PURITY OF PRODUCT IN CONTAINER: | | |
| AT TIME OF FILLING | Sterile | Sterile |
| AFTER 5 DOSES | Sterile | Sterile |
| WITH 10% LEFT IN CONTAINER | Sterile | Sterile |
| EXAMPLE | 15 | 16 |
| PRODUCT | Local Anesthetic | Local Anesthetic |
| CONTAINER | 15cc plastic squeeze bottle with dropper tip | 15cc plastic container such as shown in FIG. 1 |
| CONDITION | Various surgical conditions such as cataract extraction, suture removal & removal of foreign bodies | (Same as Example 15) |
| COMPOSITION/ ACTIVE INGREDIENTS (% by weight) | Sterile aqueous solution containing 0.5 proparacaine hydrochloride with glycerine as a stabilizer & sodium hydroxide/hydrochloride acid to adjust pH | (Same as Example 15) |
| PRESERVATIVE/ FILTER (% by weight) | Chlorobutanol & Benzalkonium chloride | None - Filter |
| POSITIONING/GUARD MEANS GENERAL CONFIGURATION (angle of positioning means to container axis) | None | Horizontal oval for vertical application (60° off axis) |
| ADMINISTRATION/ DOSAGE | Depending on type of surgery - 1 drop every 5-10 minutes for 5-7 doses | (Same as Example 15) |
| PURITY OF PRODUCT IN CONTAINER: | | |
| AT TIME OF FILLING | Sterile | Sterile |
| AFTER 5 DOSES | Sterile - discoloration starting | Sterile - no noticeable discoloration |
| WITH 10% LEFT IN CONTAINER | Sterile - but discolored | Sterile - no noticeable discoloration |
| EXAMPLE | 17 | 18 |
| PRODUCT | Irrigant | Irrigant |
| CONTAINER | 120cc irrigator bottle | 120cc irrigation bottle as shown in FIG. 15 |
| CONDITION | Use after tonometry & gonioscopy, to remove foreign bodies, wash away fluorescein solutions & mucous secretions | (Same as Example 17) |
| COMPOSITION/ ACTIVE INGREDIENTS (% by weight) | Low surface tension, sterile, stable, buffered isotonic solution of boric acid, sodium carbonate & potassium chloride | (Same as Example 17) |
| PRESERVATIVE/ FILTER (% by weight) | Benzalkonium chloride, disodium ethlenediamine tetraacetate | None - Filter |
| POSITIONING/GUARD MEANS GENERAL CONFIGURATION (angle of positioning means to container axis) | None | Vertical oval for horizontal application (90° off axis) |
| ADMINISTRATION/ DOSAGE | Use copiously as required | (Same as Example 17) |
| PURITY OF PRODUCT IN CONTAINER: | | |
| AT TIME OF FILLING | Sterile | Sterile |
| AFTER 5 DOSES | Sterile - some contaminants noted | Sterile |
| WITH 10% LEFT IN CONTAINER | Sterile - contaminants noted | Sterile |

While preferred forms and arrangements of parts have been shown in illustrating the present invention, it is to be clearly understood that various changes in details and arrangements of parts and methods may be made without departing from the spirit of the invention.

I claim:

1. The method of introducing an ophthalmic product from a dispenser into an occular cavity whereby blinking is substantially eliminated and the dispensing orifice of the dispenser does not contact said occular cavity, said dispenser comprising a container having wall means defining a cavity for containing a product to be dispensed, a dispensing orifice positioned in said wall means and in fluid communication with said cavity, and pump means constructed and arranged with said cavity to develop sufficient internal pressure within said cavity to dispense product from said cavity through said orifice, and a generally ring-shaped positioning/guard means fixedly secured to said container means and generally encircling said dispensing orifice, said positioning/guard means being angularly displaced relative to the longitudinal axis of the container, said method including the steps of positively positioning the generally ring-shaped positioning/guard means of the dispenser around the occular cavity thereby anthropometically locating the dispensing orifice relative to said occular cavity while maintaining the dispensing orifice free from interference with the normal line of sight and activating the pump means of said dispenser to dispense an effective amount of ophthalmic product into said occular cavity.

2. Method according to claim 1 wherein a prescribed concentration of ophthalmic product is introduced into a specific area of the occular cavity.

3. Method according to claim 1 wherein the product is metered.

4. Method according to claim 1 wherein the pumping action activates a pressure-responsive dispensing valve.

5. Method according to claim 1 wherein the angle of the positioning/guard means to the dispenser axis is from between 0° and about 90°.

6. A dispenser suitable for introducing an ophthalmic product into the occular cavity comprising —
   a. container means comprising
      1. wall means defining a cavity for containment of the product to be dispensed;
      2. a dispensing orifice positioned in said wall means and in fluid communication with said cavity; and
      3. a pump means constructed and arranged with said cavity to develop sufficient internal pressure within said cavity to dispense product from said cavity through said orifice; and
   b. a generally ring-shaped positioning/guard means fixedly secured to said container means and generally encircling said dispensing orifice wherein said positioning/guard means is angularly displaced relative to the longitudinal axis of the container means such that when said positioning/guard means is placed around the occular cavity said dispensing orifice can be anthropometically located relative to the occular cavity while avoiding contact with said occular cavity and interference with the normal line of sight.

7. A dispenser according to claim 6 wherein said container is provided with a pressure-responsive product dispensing valve means in fluid communication with said cavity and responsive to temporary pressure increases within said cavity, and a pressure equalizing one-way valve means in fluid communication with said cavity means, responsive to pressure differentials between said cavity and atmosphere.

8. A dispenser according to claim 7 wherein said pressure equalizing one-way valve means is provided with means for filtering air prior to the air entering said cavity means.

9. A dispenser according to claim 8 wherein the valve means is a duckbill valve.

10. A dispenser according to claim 8 wherein the valve means is a substantially non-wettable microporous material.

11. A dispenser according to claim 8 wherein the filter means is a microporous substance capable of filtering out contaminants in the air from between 0.5 and 20 microns.

12. A dispenser according to claim 6 wherein the pump means comprises a flexible wall of the cavity means.

13. A dispenser according to claim 6 wherein the generally ring-shaped positioning/guard means comprises a generally ring-shaped element which is not continuous.

14. A dispenser according to claim 6 wherein the dispensing orifice means is provided with a metering means such that from between about .01 and about 1 gram of said product is dispensed into the occular cavity with each pumping of said pumping means.

15. A dispenser according to claim 6 wherein said pump means comprises an elastomer disk in the wall of said cavity means.

16. A dispenser according to claim 6 wherein the angle of the positioning/guard means to the axis of the container is from between about 0° and about 90°.

17. A dispenser according to claim 6 wherein the angle of the positioning/guard means to the axis of the container is from between about 60° and about 75°.

18. A dispenser according to claim 6 provided with an overcap means for maintaining said dispenser orifice free from contaminants during storage and shipment.

* * * * *